United States Patent
Petteway et al.

(10) Patent No.: US 6,605,445 B1
(45) Date of Patent: Aug. 12, 2003

(54) RAPID METHOD OF DETERMINING CLEARANCE OF PRION PROTEIN

(75) Inventors: Steve R. Petteway, Cary, NC (US); Douglas C. Lee, Apex, NC (US); Robert W. Kozak, Foster City, CA (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/253,800

(22) Filed: Feb. 22, 1999

(51) Int. Cl.$^7$ .............................................. G01N 33/543
(52) U.S. Cl. .................... 435/7.92; 435/7.93; 435/7.94; 435/7.95; 435/7.1; 435/5
(58) Field of Search ...................... 438/5, 7.1; 436/536, 436/543

(56) References Cited

PUBLICATIONS

Abstract, Blood Safety and Screening Conference, Feb. 23–25, 1998, McClean, VA "Application of Western Blot Assay to Detection of PrPRES Partitioning During Selected Plasma Fractionation Process Steps." S.R. Petteway et al. Copy overheads presented at above meeting.
Transfusion vol. 38, Sep. 1998, pp. 810–816 "The Distribution of infectity in blood components and plasma derivatives in experimental models of transmissible spongiform encephalopathy." P.Brown et al.
Nature Medicine vol. 4, #10, Oct. 1998, pp. 1157–1165 "Eight prion strains have PrPsc molecules with different conformations" S. Safir et al.
Biotechnology of Blood, publisher Butterworth Heinemann, 1991, Editor: J. Goldstein, Chapter 8 Current Approaches to Plasma Fractions, J. Vandersande, pp. 165–176.

Petteway, Jr., S. R., et al., 1998, "Application of a Western blot assay to the detection of PrPRES partitioning during selected plasma fractionation process steps", Blood Safety Screening Conference, Feb. 23–25, McClean, VA.*

\* cited by examiner

*Primary Examiner*—Laurie Scheiner
*Assistant Examiner*—Jeffrey S. Parkin
(74) *Attorney, Agent, or Firm*—Mary G. Boguslaski, Esq.; Womble Carlyle Sandridge & Rice, PLLC

(57) ABSTRACT

Transmissible spongiform encephalopathies (TSEs) are a class of fatal, neurodegenerative diseases found in many mammalian species. Human TSEs include kuru, Creutzfeldt-Jakob disease (CJD), and fatal familial insomnia. Non-human TSEs include sheep scrapie, bovine spongiform encephalopathy (BSE), feline spongiform encephalopathy, and chronic wasting diseases in elk and mule deer. These neurodegenerative diseases are caused by prions and display characteristic amyloid plaque deposition. The only known component of the infectious prion is an abnormal, disease-causing isoform of the prion protein (PrP), called PrP scrapie ($PrP^{Sc}$). During a post-translational process, $PrP^{Sc}$ is formed from the normal, cellular PrP isoform ($PrP^C$). The scrapie isoform is less soluble, more proteinase-resistant, and more susceptible to aggregation than the wildtype protein. The claimed invention is directed toward a rapid, specific, sensitive, and quantitative method for the detection of TSE clearance from a plasma product utilizing a chemiluminescent Western blot immunoassay. This immunoassay format can detect picogram concentrations of $PrP^{RES}$ (proteinase resistant PrP fragment) and is linear over a 3–5 log range. The invention is useful for tracking the clearance of $PrP^{Sc}$ during plasma manufacturing processes.

22 Claims, 3 Drawing Sheets

RAPID METHOD OF DETERMINING CLEARANCE OF PRION PROTEIN

FIELD OF THE INVENTION

Figure 1:
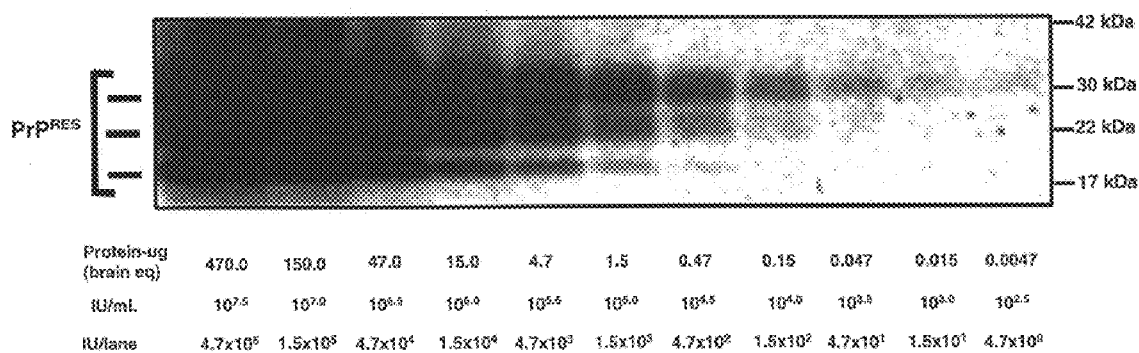

The invention relates to a rapid method of detecting pathogen or prion protein that may be use to determine the clearance of pathogen protein, in general, and to a Western blot immunoassay method of relating pathogen protein clearance to infectivity clearance, in specific. The method has been applied to the quantitation of TSE protein clearance and its relationship to infectivity clearance.

BACKGROUND OF THE INVENTION

The Cohn-Oncley purification of therapeutic proteins from blood plasma, referred to herein in general as the Cohn process or scheme, employs a series ethanol additions and pH adjustments to purify or enrich for proteins which may be used in human therapies. Commonly purified proteins include immunoglobulins, anti-hemophiliac factors and albumin. While many manufacturers of such products utilize the basic Cohn scheme, frequently established steps may be modified or additional steps are implemented to increase either the purity and/or yield for a given product. Such steps are typically proprietary for a given manufacturer.

Since the discovery that HIV could be carried and transmitted though the use of blood products, the interest and concern about the presence of such pathogenic agents in biological products derived from blood has increased. Most recently, there has been concern that CJD, Creutzfeldt-Jakob Disease, could be transmitted through the use of blood-derived product. CJD is one of the human transmissible spongiform encephalopathies (TSE), a collection of neurodegenerative diseases that are debilitating and fatal. Infectivity associated with CJD appears to be either associated with or caused by the prion protein (PrP). Although new disease carrying viruses may be generated at any time, manufacturers of blood-based products take precautions to obtain a blood product that is free of known transmissible diseases, to the extent for which these can be tested. Unfortunately, the primary test for possible TSE infectivity is a biological assay in which rodents are injected with the material of interest to see if infectivity develops. The results of such assays require nine months to a year to develop, frequently too long to hold a manufactured lot of plasma product prior to release for use.

Therefore, a method of detecting a protein associated with a pathogen suspected of carrying infectivity such as the prion or viral surface (coat) protein is important for the blood fractionation industry. A rapid, sensitive method capable of determining the removal of virus or pathogenic prion protein would provide the blood fractionation industry with a useful tool for determining what danger of infectivity exists after a particular manufacturing process step. The decrease in viral or prion protein relative to a given product associated with a manufacturing process step is referred to herein as "clearance". Because of the importance of such a test for TSE infectivity to the safety of plasma products, the method of this invention was described generally at the Blood Safety and Screening conference held in McClean, Va. on Feb. 23, 1998.

SUMMARY OF THE INVENTION

The invention is an immunoassay method of detecting viruses or prion protein content of a biological sample. This method provides a quantitative measure of the viral or prion protein content that may be related to infectivity. The method an typically detect a range of prion protein from 3 logs to 5 logs dynamic range and the measured clearance correlates well with infectivity clearance for the process steps have been tested. The preferred immunoassay method is a Western blot and results are available in 2–4 days. The method is particularly useful to track the prion protein related to potential infectivity in plasma production.

The method of the invention is composed of the steps of preparing: a) a biological sample, usually a plasma or plasma manufacturing intermediate sample, for an immunoassay, either a Western blot immunoassay or an ELISA immunoassay; b) performing the immunoassay for the protein associated with infectivity; c) quantitating the protein results; and, d) relating the protein results to infectivity. Preferably the quantitative method employs a Western blot immunoassay method. This method may be used to determine clearance of the pathogenic protein in a biological sample such as a plasma product or plasma processing sample by preparing an aliquot of a first sample; performing the Western blot assay on such first sample; quantitating the pathogenic protein results in the first sample; processing the first sample to obtain a second sample or samples from the process stream of the first sample; performing and quantitating the pathogenic protein results from the second sample or samples and comparing relative amounts of pathogenic protein detected in the first and second sample to determine the clearance of the processing step.

An application of particular interest is determining the clearance of TSE by a particular plasma processing step. The comparative quantitative results of the two immunoassays provide a measure of the "clearance" obtained by the processing step.

The preferred method is composed of the following steps:
 a. spiking a process solution with a brain homogenate from an animal infected with the pathogen marker (typically a protein) of interest;
 b. processing the spiked solution; and
 c. assaying for the presence of the pathogen protein marker (prion protein) in the resulting fractions for distribution of the protein.

The assay step is composed of the following steps:
 a. taking a sample of each fraction of interest;
 b. diluting the samples in defined increments;
 c. treating each diluted sample with proteinase-K;
 d. (optionally) centrifuging the proteinase-K treated samples; and
 e. performing a Western blot or ELISA immunoassay.

The preferred Western blot immunoassay is composed of the following steps:
 a. separating the proteinase K treated samples electrophoretically;
 b. transferring the separated samples to a membrane;
 c. adding a blocking agent to the membrane containing the separated samples;
 d. incubating the membranes with a first antibody capable of binding the pathogenic protein;
 e. washing the incubated membrane with a low salt buffer to remove any non-binding antibodies and proteins;
 f. incubating the washed membrane with a second antibody capable of recognizing the first antibody, which second antibody contains a reporter group capable of providing a measurable signal; and g. measuring the signal produced by counting the number of lanes with detectable signal.

The number of lanes with detectable protein from sample diluted in defined increments allows for the estimation of infectivity clearance for a sample when compared to the spiked input material (prove). For the TSE protein assay, a preferred first antibody is the monoclonal antibody, 3F4.

DETAILS OF THE INVENTION

Determining the risk of transmission by blood or plasma-derived products of an infective virus or prion protein requires sensitive and specific assays for the detection of either infectivity or a reasonable marker for infectivity. This invention provides an immunoassay that fulfills all criteria: sensitive, specific, fast and low cost. Described in detail herein is one application of the invention, a Western blot immunoassay, that is both sensitive and reproducible for the detection of $PrP^{RES}$, a marker for transmissible spongiform encephalopathy (TSE) infectivity. One of skill in the art of such assays will be able to apply the method provided to the determination of the risk of transmission of other types of infectivity.

The method of the invention utilizes an immunologically-based assay, such as a Western blot or an ELISA technique, to monitor for the presence of the pathogenic form of the prion protein through a manufacturing process of a plasma- or biologically-derived product. The preferred method of the invention utilizes a sensitive Western blot immunoassay to detect the pathogenic form of PrP ($PrP^{Sc}$), referred to herein at times as TSE protein, in a series of carefully made dilutions made from samples containing an unknown amount of PrP. The invention involves spiking of a plasma process solution with the brain homogenate from an infected animal (such as hamster, mouse, sheep or human) that contains the pathogenic prion protein ($PrP^{Sc}$). An aliquot is removed for analysis (prove sample) and the remaining material is processed. Upon completion of the process step, the resulting fractions, typically an effluent (or liquid fraction) and a precipitate (or solid fraction), are obtained. The solid fraction is resuspended in an appropriate buffer such as phosphate buffered saline (PBS) or tris buffered saline (TBS) to the same volume as the other samples. All samples (prove, effluent and precipitate) are diluted in defined increments (e.g. 0.5 logs or 1 log steps) and each are treated with proteinase K to remove the non-pathogenic prion ($PrP^{C}$) and other proteins that may cross-react and interfere with the PrP signal. In some cases these proteinase-K treated dilutions are centrifuged and the resulting pellet contains more concentrated PrP. If the Western blot is used, the samples to be analyzed are electrophoretically separated and then transferred to a membrane (such as nitrocellulose or PVDF). These membranes are blocked in the presence of (a) blocking agent(s) which may include but not be limited to, non-fat dried milk, serum albumin or casein. The membranes are incubated in the presence of either a monoclonal or polyclonal antibody, the "first antibody", then washed with a low salt buffer to remove non-binding antibodies and proteins. The washed membranes are then incubated with a second antibody or antibodies that recognize the first antibody. The second antibody has a reporter group attached for the visualization of the first antibody. This reporter that is attached to the second antibody may be either a chemical "tag" or an enzyme (such as alkaline phosphatase, horseradish peroxidase) that catalyzes a reaction that converts an added substrate to a product that is visualized. The method of visualization may include chemiluminescent, fluorescence or colorimetric technologies. For the specific TSE assay given herein the preferred visualization method is chemiluminescent and based on a alkaline phosphatase reporter conjugated to the second antibody. If the assay employed is similar to an ELISA, the electrophoretic separation and membrane transfer is omitted and the assay is performed in a ELISA plate. Quantitation of the clearance assay employs a quantal format which compares the resulting positive lanes (Western blot) or wells (ELISA) detected for the input (prove) sample with one or more of the output fractions (e.g. paste and/or effluent).

This method differs from prior art in that it does not use the rodent bioassay to follow infectivity partitioning in process steps (Brown et al., Transfusion, Vol. 38, September 1998). By detecting the pathogenic subform of the prion protein, $PrP^{Sc}$, rather than monitoring for infectivity, the method saves a significant amount of time and money.

The method of the invention is exemplified in detail below for the important TSE assay. The assay is based on the identification of a marker protein, $PrP^{Sc}$, with the disease infectivity and the use of an antibody to that prion protein. The specific primary antibody used herein is the monoclonal antibody designated 3F4 which may be obtained from Dr. Richard Rubenstein at the New York Institute for Basic Research in Developmental Disabilities, Staten Island, N.Y. or from Chemicon, Temecula, Calif.

Preferred Embodiment

To assess the risk of TSE disease transmission in manufacturing processes for biological products, a sensitive in vitro assay was used as a predictive tool for tracking infectivity in plasma purification processes. The method of this invention is a sensitive, robust Western blot assay which is specific detection of $PrP^{RES}$ (the proteolytically derived "core" or $PrP^{Sc}$) and therefore may be used to monitor the partitioning of $PrP^{Sc}$. The method of the invention has been successfully used to monitor the partitioning of $PrP^{Sc}$ through three plasma protein purification steps critical to the isolation of various plasma therapeutics.

A major advantage of the Western blot format rather than other in vitro formats is the electrophoretic separation step that precedes immunologic detection. The Western blot image for $PrP^{RES}$ demonstrates a distinct "fingerprint" of three protein bands of molecular masses ranging from 20 kD to 30 kD. The detection of these bands serves as visual confirmation that the signal observed is derived from $PrP^{RES}$. In addition to this protein "fingerprint", the Western blot employs both antibody specificity and proteinase-K (PK) resistance of $PrP^{Sc}$ to further insure assay reliability.

The Western blot assay of this invention is more sensitive than other assays described in the literature including dot blot, various ELISA systems, as well as other Western blot systems. In 1990 a dot blot assay format was used to detect $PrP^{Sc}$, but only with qualitative results. The dot blot assay, however, did not use the sensitive chemiluminescent detection system employed in this invention. As presented here, $PrP^{Sc}$ may be detected in as little as 10. nanograms (ng) of brain equivalents. Other groups have reported Western blot detection systems for detecting PrP in brain homogenates detecting to 2.5 micrograms ($\mu$g) brain equivalents. Western blot systems using spleenic tissue as the starting material demonstrated detection of $PrP^{Sc}$ in as little as 0.3 mg material following treatment with collagenase. In a recent paper, Safar and co-workers (J. Safar et al., Nature Medicine, Vol 4, No. 10, October 1998) describe a conformation dependent ELISA reportedly able to distinguish various PrP conformers equating to various scrapie strains.

The authors claim a sensitivity approximately $10^3$ IU/ml, within the range of the Western blot assay of this invention.

A different series of studies, Brown and co-workers (ibid) using both spiked and endogenous plasma infectivity models looked at partitioning of model TSEs in several plasma processing steps. In contrast to the method of this invention which monitors for quantity of $PrP^{Sc}$, Brown et al monitored actual infectivity. While some of their results are consistent with those found with the method of this invention, the comparison is complicated by the difference in plasma fractionation processes from which the samples were derived and by the fact that a significant amount of input infectivity was not recovered.

In conclusion, the Western blot assay of this invention has been demonstrated to be a robust and sensitive assay for the prion protein. The overall goal of these efforts was to develop an assay that could correlate with TSE infectivity in order to predict infectivity. In hamster brain homogenates, the method is routinely able detect to 5 pg of $PrP^{RES}$ or where infectivity is as low as $10^3$ IU/ml. This invention provides an inexpensive and rapid assay for the assessment of TSE partitioning in protein purification steps that are used for the production of plasma-derived therapeutics. Previously the rodent bioassay has been used to determine partitioning of infectivity. However, such studies are time consuming and expensive to perform. Immunologically based assays for the detection of $PrP^{RES}$ have been used as a diagnostic marker for TSE infection. These assays rely on the close association of $PrP^{Sc}$ with TSE infectivity.

Western Blot Immunoassay for the Determination of TSE

Several molecular markers for TSE have been identified. However, the most frequently cited are the structural changes observed in the normal (cellular) prion protein ($PrP^c$) which undergoes significant alterations in both secondary and tertiary structures in the diseased state. The ensuing changes have such significant consequences on the physicochemical nature of the PrP molecule, that a novel entity of the $PrP^c$ molecule results and is designated $PrP^{Sc}$ (prion protein, scrapie form). The $PrP^{Sc}$ isoform is less soluble in aqueous buffers, and more proteinase resistant than its $PrP^c$ counterpart. Treatment of $PrP^{Sc}$ with proteinase-K (PK) results in the removal of only 90 amino acids from the N-terminus. The remaining PrP "core" is denoted $PrP^{RES}$ (prion protein, proteinase resistant). Several studies suggest that the $PrP^{Sc}$ isoform is the infectious agent for TSEs and that it is necessary for disease transmission.

Using the 263 K hamster strain of TSE as a model system, the assay is sensitive, specific and linear over a 3–5 log dynamic range. Compared to the rodent bioassay, the assay was shown to detect $PrP^{RES}$ in approximately $10^{3,4}$ IU/ml which equates to approximately 5 pg of PrP or 8 ng brain equivalents. The Western blot method described herein was used to monitor the partitioning of $PrP^{Sc}$ through three plasma fractionation steps, Cryoprecipitation, Fraction I and Fraction III, that are common to the purification of several plasma-derived therapeutic products including albumin and immunoglobulins. The results from these studies demonstrated a 1 log, 1 log and 4 logs of $PrP^{Sc}$ partitioning away from the effluent fraction. Bioassays for TSE infectivity confirmed the results.

The Western blot immunoassay provided allows for the detection of $PrP^{RES}$ in less than 10 nanograms (ng) of brain tissue or to the limit of approximately 5 picograms (pg) of $PrP^{RES}$. This level of detection corresponds to the detection of $PrP^{RES}$ in samples where infectivity is not greater than $10^3$ Infectious Units per milliliter (IU/ml). The method utilizes chemiluminescence technology to visualize PrP on the Western blot membranes and requires nominal sample manipulation. The assay is robust and reproducible and may be performed in most laboratories with minimal equipment expenditures. The Western blot assay is able to follow the partitioning of $PrP^{Sc}$ through three protein purification steps that are commonly used for the isolation of several plasma-derived therapeutics.

Materials and Methods

Preparation of brain homogenates: Ten percent scrapie brain homogenates (SBH) were prepared using hamster brains infected with the 263 K hamster-adapted agent. Previously frozen hamster brains were allowed to thaw on ice and weighed. Nine volumes of ice-cold Tris buffered saline (TBS) were added and the mixture homogenized using a Polytron apparatus followed by Dounce homogenization using a B pestle. Normal brain homogenates (NBH) were prepared similarly except 25 micromolar ($\mu$M) 4-(2-aminoethyl) benzenesulfonyl fluoride (AEBSF) was present to inhibit endogenous proteinase activity. Homogenates were stored at −70° C.

Sample Preparation I—Standard Dilution Protocol: A serial dilution on 0.5 log scale was made by mixing 315 microliter ($\mu$l) of sample with 684 $\mu$l of 0.1 ml bovine serum albumin (BSA) prepared in phosphate buffered saline (PBS) for the samples to be tested. From each, 80 ml was withdrawn and incubated with 350 $\mu$g/ml PK for 1 hour at 37° C. To terminate the PK reaction, AEBSF was added to a final concentration of 10 millimolar (mM) and incubated for 10 minutes at ambient temperature. An equal volume of 2X SDS PAGE sample buffer (Novex, San Diego, Calif.) was added and each sample was heated to 100° C. for 10 minutes. In general, 15 ml/well of these solutions were loaded on the gel for analysis. In some cases it was necessary to perform this dilution series in 0.1 ml volumes. For these, the diluents were adjusted accordingly.

Sample Preparation II—Centrifugation Method to Concentrate the PrP Signal: During the course of these studies, it was determined that using high speed centrifugation increased the sensitivity of the Western blot assay. To this end, the samples were diluted and treated with PK followed by AEBSF as described above. Following the PK treatment, the vials were centrifuged at 20,000 xg for one hour at 4° C. in a fixed angle rotor. The pellet was resuspended in 10 ml of 2X SDS-PAGE sample buffer (Novex), heated for 10 min at 95° C. and the entire sample was electrophoresed.

Polyacrylamide Gel Electrophoresis (PAGE): Samples prepared by either method were electrophoresed on 8.3 cm×7.5 cm, 1.0 mm, 12% SDS-Tris-glycine polyacrylamide gels (Novex Cat# EC60055) for 60 minutes at 125 constant volts.

Western Blot Assay: All volumes described were optimized for the Novex (San Diego, Calif.) gel system using only a single gel or membrane. Improved transfers were obtained when a single gel was blotted per transfer unit. Proportionate increase in working solution volumes are required with additional membranes. Unless otherwise stated, all manipulations were performed at room temperature (22°–25° C.) using molecular biology grade reagents.

Nitrocellulose membranes (0.45 $\mu$m, Novex) were soaked in Novex transfer buffer for 5–10 minutes prior to "sandwich" assembly. The transfer from the gel to the nitrocellulose membrane was performed for 60 minutes at 125 milliAmps (mA). Following transfer, the membranes were soaked in TBS (pH 8.0) for 5–10 minutes. The membranes were blocked for 60 minutes in 5% non-fat milk (Organic Valley, CROPP Cooperative, LaFarge, Wis.) dissolved in TBST (TBS with 0.05% Tween) with gentle agitation. Following blocking, the membranes were incubated in a 1:10,000 dilution of 3F4 monoclonal antibody diluted in blocking buffer overnight (12–18 hours) at 4° C. The membranes were rinsed three times with TBST and washed three times for 5 minutes per wash. The membranes were incubated at room temperature for 90 minutes with anti-mouse alkaline phosphatase-conjugated IgG (Catalogue #AMI0405, BioSource International or Catalogue #108004, Southern Biotechnologies Associates, Inc.) at a 1:10,000 dilution in 20 ml of 5% blocking buffer. Following incubation in the secondary antibody, the membranes were rinsed with 3 changes of TBST, then washed in TBST for 60 minutes.

The membranes were agitated for 60 minutes in 50 ml assay buffer (10 mM Tris, 200 $MgCl_2$, pH 10.0), blotted dry, incubated with 3 ml CDP-Star (Tropix, Bedford, Mass.), containing 0.15 ml NitroBlock II (Tropix, Bedford, Mass.) and were laid on a Whatman 3MM filter paper. The blots were placed in a developing folder (Tropix, Bedford, Mass.) and transferred into a film cassette. The membranes were exposed to film (Kodak XAR-2 or Fuji RX). Generally, exposures of 5, 15, 30, and 60 minutes were obtained, although 90–120 minutes exposures were possible.

Western Blot Quantitation: Unlike previously employed assay, the Western Blot method of this invention has been developed to provide quantitative results. Quantitation of the Western blot films employs an endpoint dilution of a characterized brain homogenate to quantitate infectivity in a solution containing unknown amount of $PrP^{Sc}$ similar to that described for viral assays. This is performed by spiking a known amount of hamster brain homogenate into a given solution that is to be subjected to the manufacturing process. An aliquot is removed prior to performing the manufacturing process and is designated the "prove" sample. The manufacturing step is performed and the resulting fractions are retained for Western blot analysis. Typically two fractions are obtained; a solid, precipitate, fraction and a liquid, effluent fraction. The solid is resuspended in PBS with 0.1% BSA to the same volume as the prove. The prove and/or the liquid fraction is adjusted similarly using the same diluent. The samples are carefully diluted as described above and subjected to Western blot analysis.

For each sample that has been diluted and assayed, a comparison is made to compare the number of detectable lanes. Typically, dilutions are made in 0.5 log increments; therefore, if 10 lanes (Western blot) or wells (ELISA) react positively for $PrP^{RES}$, the sample is said to have 5 logs of prion detection.

Plasma Fractionation Studies: All plasma fractionations were performed based on the original methods of Cohn. The resulting pellets and effluents were reconstituted to equal volumes for comparison in the Western blot. It has been demonstrated that this assay can be used to monitor the distribution of $PrP^{Sc}$ in samples obtained from three plasma fractionation processes.

Results

This Western blot system has the potential to measure the target protein to a level equivalent of infectivity as low as $10^3$ IU/ml or approximately 5 pg $PrP^{RES}$ in dilutions derived from infectious brain homogenates (FIG. 1). This level of detection corresponds to PrP detection approaching 10 ng of brain tissue equivalents. Specificity of the Western blot was confirmed using a peptide that mimicked the 3F4 epitope on PrP which effectively competed for the PrP signal. The assay was demonstrated to be reproducible by having multiple analysts perform the assay with consistent results.

Figure 2:
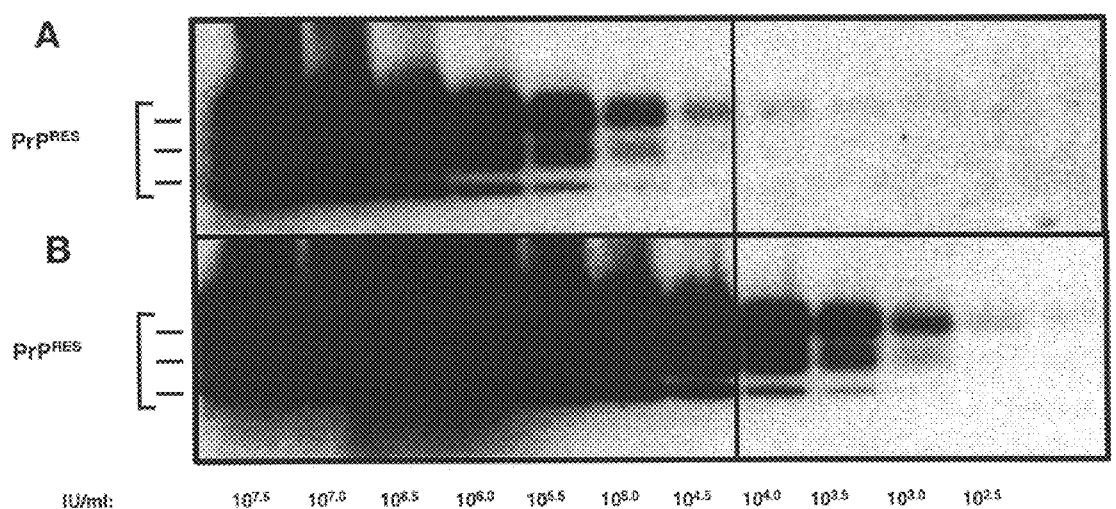

Optional: Method II: Sometimes, the $PrP^{RES}$ signal was interfered with in certain plasma fractionated samples due to the presence of exogenous proteins. To overcome this impediment, a second protocol (Method II) was developed that employed a high speed centrifugation of the PK-treated dilutions to concentrate the $PrP^{RES}$. The resulting pellets, enriched for $PrP^{RES}$, were solubilized with SDS-PAGE sample buffer, and the entire pelleted sample was subjected to Western blot analysis. FIG. 2 shows the enhancement in $PrP^{RES}$ signal in SBH samples following this approach. This treatment increased the sensitivity or $PrP^{RES}$ detection by approximately 1.5 logs and after development was used in all subsequent fractionation steps studied and is the preferred mode of practicing the invention.

The detection of $PrP^{RES}$ by Western blot was compared to infectivity using the rodent bioassay. A sample of SBH was serially diluted in 0.5 log increments using both standard and centrifuged dilution protocols and analyzed using the Western blot. Aliquots only from the standard dilution protocol were subjected to the bioassay (Table I). The undiluted 10% SBH used in this study was determined to have a titer of $10^{7.9}$ IU/ml by the rodent bioassay. The Western blot detected $PrP^{RES}$ immunoreactivity equating to $10^{4.4}$ IU/ml infectivity in samples derived from the standard sampling procedure. The centrifugation protocol allowed detection of $PrP^{RES}$ in as few as $10^{3.4}$ IU/ml of sample homogenate. Since performing this specific experiment, further progress has allowed us to improve $PrP^{RES}$ detection in as little as $10^3$ IU/ml.

To address the issue of diluents and their impact on the dilution properties of $PrP^{Sc}$, several dilution mediums were tested including PBS, TBST, sarkosyl, human plasma, BSA and hamster NBH. The sensitivity of the Western blot assay was dependent on the diluent used for sample preparation. Of all the diluents tested, BSA was the most effective at maintaining linearity of dilution, while still retaining the greatest sensitivity.

0.5 to 1 log differences in $PrP^{RES}$ levels can be readily discerned with the Western blot assay. Application of the Western blot to the measurement of $PrP^{Sc}$ disposition through plasma processing can be quantitated and compared to data obtained from bioassay analysis.

FIGURE LEGENDS

FIG. 1. Demonstration of sensitivity of assay system using the Western blot protocol. Hamster SBH was diluted in 0.1% BSA/PBS in 0.5 log increments, treated with PK and subjected to Western blot analysis as described in the Materials and Methods. The numbers below the panel illustrate the relative amounts of putative infectivity in the corresponding dilution (IU/ml) or as related to the volume loaded on the gel (IU/lane).

FIG. 2. Centrifugation concentrates the $PrP^{Sc}$ signal and increases the number of lanes detected in Western blots. (A) 0.5 log dilutions of SBH generated using standard dilution methods as described in Materials and Methods. (B) The remaining dilutions generated for (A) were concentrated by centrifugation. The resulting pellets were subjected to Western blot analysis and demonstrate an increase in the level of detection.

Figure 3:
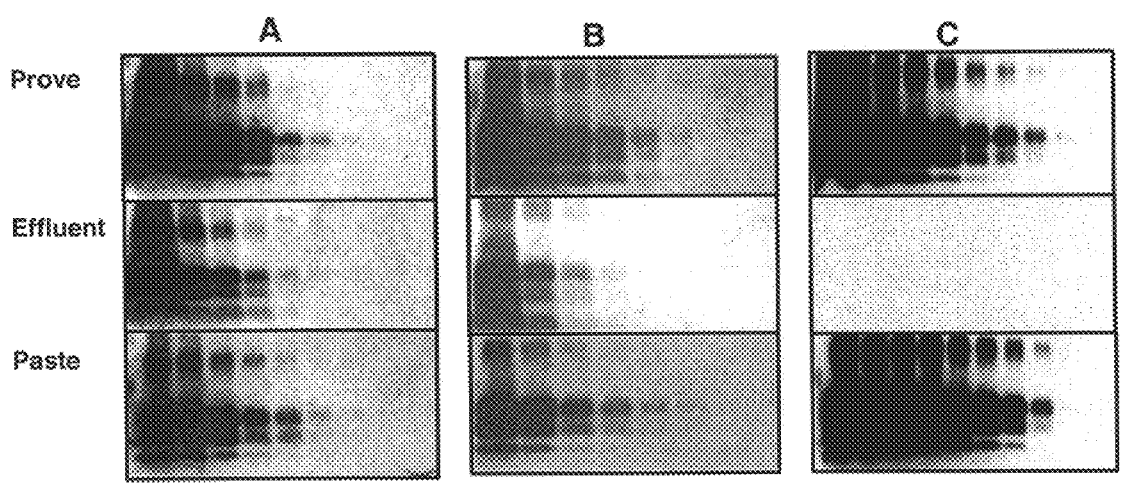

FIG. 3. Application of the Western blot to the analysis of the plasma processing steps. SBH spiked Cryoprecipitate (A), Fraction I (B) and Fraction III (C) steps generated Prove, Effluent and Paste samples which were subjected to Western blot analysis.

TABLE I

Direct comparison of Western blot data with bioassay.
Sample of SBH were diluted in 0.5 log increments.
Each dilution was analyzed using the Western blot assay,
while every other dilution was analyzed in the rodent bioassay.
Analysis of the data derived from the bioassay demonstrates that
the infectivity titer of the undiluted SBH to
be $10^{7.9}$ IU/ml. Western blot lanes positive for
PrP$^{RES}$ signal are designated with a plus
(+) sign, negative lanes are designated with a minus (−) sign.

|  | Western blot | | Bioassay Results. | | |
|---|---|---|---|---|---|
| SBH Dilution | Standard Method | Centrifuged Method | Dead/total | Incubation (days) | IU/ml |
| 0 | + | + | ND | ND | $10^{7.9}$ |
| −0.5 | + | + | ND | ND | $10^{7.4}$ |
| −1.0 | + | + | 5/5 | 72 ± 2 | $10^{6.9}$ |
| −1.5 | + | + | ND | ND | $10^{6.4}$ |
| −2.0 | + | + | 5/5 | 80 ± 2 | $10^{5.9}$ |
| −2.5 | + | + | ND | ND | $10^{5.4}$ |
| −3.0 | + | + | 5/5 | 86 ± 2 | $10^{4.9}$ |
| −3.5 | + | + | ND | ND | $10^{4.4}$ |
| −4.0 | − | + | 5/5 | 91 ± 1 | $10^{3.9}$ |
| −4.5 | − | + | ND | ND | $10^{3.4}$ |
| −5.0 | − | − | 4/5 | 97 ± 0 | $10^{2.9}$ |
| −5.5 | ND | − | ND | ND | $10^{2.4}$ |
| −6.0 | ND | ND | 5/5 | 117 ± 6 | $10^{1.9}$ |
| −6.5 | ND | ND | ND | ND | $10^{1.4}$ |
| −7.0 | ND | ND | 1/5 | 125 | $10^{0.9}$ |
| −7.5 | ND | ND | ND | ND | $10^{0.4}$ |
| −8.0 | ND | ND | 0/5 | 0/5 | — |

ND, not determined

What is claimed is:

1. A quantitative Western blot immunoassay method useful for the determination of TSE protein clearance during the processing of plasma products, comprising the steps of:
   a) preparing an aliquot of a relevant first sample chosen from plasma or a processed plasma sample for a Western blot immunoassay;
   b) performing the Western blot assay for TSE protein on such first sample;
   c) quantitating TSE protein in the first sample aliquot;
   d) submitting the first plasma sample or first processed plasma sample to a processing treatment producing a second sample;
   e) performing a Western blot assay for TSE protein on an aliquot of the second sample;
   f) quantitating TSE protein results in the second sample; and
   g) comparing the quantitative TSE protein in the first sample to the quantitative TSE protein in the second sample to determine if the processing step provides detectable TSE protein clearance.

2. A method of determining TSE protein clearance by a particular plasma processing step:
   a) taking a sample of plasma paste prior to the processing step of interest; performing a Western blot analysis on the plasma paste sample to quantitate TSE protein content;
   b) spiking the plasma paste with known amount of scrapie brain homogenate; resuspending the spiked paste;
   c) taking an aliquot of the resuspended spiked paste; and performing a Western blot analysis on the resuspended spiked paste to quantitate TSE protein content;
   d) performing the processing step of interest on the plasma paste thereby obtaining a processed paste and an effluent;
   e) taking a sample of the processed paste and performing a Western blot analysis to quantitate TSE protein content in the processed paste;
   f) comparing TSE protein content of the samples tested to determine if satisfactory TSE protein clearance has been obtained.

3. The method of claim 1 wherein the samples are prepared by:
   a) diluting with a physiologically compatible buffer to form a buffered dilution; and
   b) treating the buffered dilution with proteinase-K to form a buffered proteinase-K dilution.

4. The method of claim 3 wherein the sample is diluted serially, up to nine logs.

5. The method of claim 3 wherein the physiologically compatible buffer is a buffered saline solution.

6. The method of claim 5 wherein the buffer component of the buffered saline solution is chosen from the group consisting of PBS, 0.1% BSA in PBS, and Tris buffered saline.

7. The method of claim 3 wherein an aliquot of the diluted sample is treated with proteinase-K.

8. The method of claim 7 wherein the proteinase-K treated dilution is concentrated.

9. The method of claim 8 wherein the proteinase-K treated dilution is concentrated by centrifugation of filtration.

10. The method of claim 9 wherein the concentrated proteinase-K treated solution is resuspended and subjected to Western blot immunoassay, comprising the steps of:
    a) separating the proteinase-K treated samples electrophoretically;
    b) transferring the separated samples to a membrane;
    c) adding a blocking agent to the membrane containing the separated samples;
    d) incubating the membranes with a first antibody capable of binding to TSE protein;
    e) washing the incubated membrane with a low salt buffer to remove any nonbinding antibodies and proteins;
    f) incubating the washed membrane with a second antibody capable of recognizing the first antibody, which second antibody contains a reporter group capable of providing a measurable signal; and
    g) measuring the signal produced by counting the number of lanes with a detectable signal.

11. The method of claim 10 wherein the Western blot immunoassay utilizes the monoclonal antibody, 3F4, as the first antibody for the identification of the TSE protein on the membrane.

12. The method of claim 11 wherein the results of the Western blot are quantified by:
    a) determining the number of immunoreactive lanes on the membrane that contain a signal attributable to the presence of TSE protein; and
    b) approximating the amount of TSE protein present to the limits of detection.

13. The method of claim 2 wherein the samples are prepared by:
    a) diluting with a physiologically compatible buffer to form a buffered dilution; and
    b) treating the buffered dilution with proteinase-K to form a buffered proteinase-K dilution.

14. The method of claim 13 wherein the sample is diluted serially, up to nine logs.

15. The method of claim 13 wherein the physiologically compatible buffer is a buffered saline solution.

16. The method of claim 15 wherein the buffer component of the buffered saline solution is chosen from the group consisting of PBS, 0.1% BSA in PBS, and Tris buffered saline.

17. The method of claim 13 wherein an aliquot of the diluted sample is treated with proteinase-K.

18. The method of claim 17 wherein the proteinase-K treated dilution is concentrated.

19. The method of claim 18 wherein the proteinase-K treated dilution is concentrated by centrifugation or filtration.

20. The method of claim 19 wherein the concentrated proteinase-K treated solution is resuspended and subjected to Western blot immunoassay, comprising the steps of:
   a) separating the proteinase-K treated samples electrophoretically;
   b) transferring the separated samples to a membrane;
   c) adding a blocking agent to the membrane containing the separated samples;
   d) incubating the membranes with a first antibody capable of binding to TSE protein;
   e) washing the incubated membrane with a low salt buffer to remove any nonbinding antibodies and proteins;
   f) incubating the washed membrane with a second antibody capable of recognizing the first antibody, which second antibody contains a reporter group capable of providing a measurable signal; and
   g) measuring the signal produced by counting the number of lanes with a detectable signal.

21. The method of claim 20 wherein the Western blot immunoassay utilizes the monoclonal antibody, 3F4, as the first antibody for the identification of the TSE protein on the membrane.

22. The method of claim 21 wherein the results of the Western blot are quantified by:
   a) determining the number of immunoreactive lanes on the membrane that contain a signal attributable to the presence of TSE protein; and
   b) approximating the amount of TSE protein present to the limits of detection.

* * * * *